(12) United States Patent
Ouchi

(10) Patent No.: US 11,045,078 B2
(45) Date of Patent: Jun. 29, 2021

(54) TREATMENT INSTRUMENT INSERTION TOOL

(71) Applicant: OLYMPUS CORPORATION, Tokyo (JP)

(72) Inventor: Naoya Ouchi, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 573 days.

(21) Appl. No.: 15/972,293

(22) Filed: May 7, 2018

(65) Prior Publication Data

US 2018/0249899 A1    Sep. 6, 2018

Related U.S. Application Data

(63) Continuation of application No. PCT/JP2016/081670, filed on Oct. 26, 2016.

(30) Foreign Application Priority Data

Nov. 16, 2015 (JP) .............................. JP2015-223938

(51) Int. Cl.
*A61B 1/018* (2006.01)
*G02B 23/24* (2006.01)
(Continued)

(52) U.S. Cl.
CPC ............ *A61B 1/018* (2013.01); *A61B 1/0014* (2013.01); *A61B 1/00087* (2013.01);
(Continued)

(58) Field of Classification Search
CPC .......................... A61B 1/0014; A61B 1/00133
See application file for complete search history.

(56) References Cited

U.S. PATENT DOCUMENTS 7,060,025 B2 *  6/2006  Long .................... A61B 1/0014
                                                        128/898
8,083,669 B2 * 12/2011  Murakami ......... A61B 1/00059
                                                        600/106
(Continued)

FOREIGN PATENT DOCUMENTS

JP       2007-089808 A       4/2007
JP       2010-022619 A       2/2010
(Continued)

OTHER PUBLICATIONS

International Search Report dated Jan. 24, 2017 issued in PCT/JP2016/0816870.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

A treatment instrument insertion tool includes a main body section, an attachment portion configured to attach the main body section to an insertion section, a guide section that is connectable to a treatment instrument insertion port of an endoscope, and that is configured to guide a treatment instrument extending from the main body section into the insertion section through the treatment instrument insertion port, and an operation member that is provided on the main body section, that can fix the treatment instrument that is inserted in the main body section, by being at least partially elastically deformed, and that is configured to perform an operation of moving the treatment instrument forward or backward along a direction of an axis of the treatment instrument and an operation of rotating the treatment instrument around the axis in a fixed state in which the treatment instrument is fixed.

11 Claims, 7 Drawing Sheets

(51) Int. Cl.
  *A61B 1/00* (2006.01)
  *A61B 17/29* (2006.01)
  *A61B 17/00* (2006.01)
  *A61B 17/221* (2006.01)
  *A61B 90/50* (2016.01)
  *A61B 1/005* (2006.01)

(52) U.S. Cl.
  CPC ...... *A61B 1/00133* (2013.01); *A61B 17/2909* (2013.01); *G02B 23/24* (2013.01); *G02B 23/2476* (2013.01); *A61B 1/0055* (2013.01); *A61B 17/00234* (2013.01); *A61B 17/221* (2013.01); *A61B 90/50* (2016.02); *A61B 2017/00296* (2013.01); *A61B 2017/00469* (2013.01); *A61B 2017/2905* (2013.01)

(56) References Cited

U.S. PATENT DOCUMENTS

| | | | | |
|---|---|---|---|---|
| 9,155,551 B2* | 10/2015 | Kuroda | | A61B 17/221 |
| 2001/0025174 A1* | 9/2001 | Daniel | | A61B 1/00179 |
| | | | | 606/15 |
| 2003/0176766 A1* | 9/2003 | Long | | A61B 1/0014 |
| | | | | 600/106 |
| 2003/0176767 A1* | 9/2003 | Long | | A61B 1/0014 |
| | | | | 600/106 |
| 2005/0234297 A1* | 10/2005 | Devierre | | A61B 1/00098 |
| | | | | 600/153 |
| 2006/0252993 A1* | 11/2006 | Freed | | A61M 25/0147 |
| | | | | 600/146 |
| 2007/0078301 A1* | 4/2007 | Kura | | A61B 10/06 |
| | | | | 600/106 |
| 2007/0129719 A1* | 6/2007 | Kendale | | A61B 1/00101 |
| | | | | 606/41 |
| 2007/0282305 A1* | 12/2007 | Goldfarb | | A61B 1/01 |
| | | | | 604/528 |
| 2008/0188868 A1* | 8/2008 | Weitzner | | A61B 1/018 |
| | | | | 606/130 |
| 2010/0022826 A1* | 1/2010 | Akahoshi | | A61B 17/2909 |
| | | | | 600/104 |
| 2010/0081874 A1* | 4/2010 | Miyamoto | | A61B 1/0051 |
| | | | | 600/109 |
| 2010/0125164 A1* | 5/2010 | LaBombard | | A61B 1/00101 |
| | | | | 600/104 |
| 2010/0217072 A1* | 8/2010 | Kondoh | | A61B 1/00101 |
| | | | | 600/101 |
| 2011/0099773 A1* | 5/2011 | Golden | | A61B 1/00128 |
| | | | | 24/457 |
| 2011/0172490 A1* | 7/2011 | Ishikawa | | A61B 1/0014 |
| | | | | 600/102 |
| 2012/0046523 A1* | 2/2012 | Yamakawa | | A61B 1/00133 |
| | | | | 600/118 |
| 2013/0237753 A1* | 9/2013 | Mark | | A61B 1/018 |
| | | | | 600/104 |
| 2013/0317515 A1* | 11/2013 | Kuroda | | A61B 10/0266 |
| | | | | 606/113 |
| 2014/0166023 A1* | 6/2014 | Kishi | | G06F 3/01 |
| | | | | 128/849 |
| 2014/0221739 A1* | 8/2014 | Yamada | | A61B 17/00234 |
| | | | | 600/106 |
| 2014/0223701 A1* | 8/2014 | Bean | | A61B 1/00133 |
| | | | | 24/483 |
| 2015/0045617 A1* | 2/2015 | Yamada | | A61B 1/00128 |
| | | | | 600/106 |
| 2015/0057537 A1* | 2/2015 | Dillon | | A61B 1/0125 |
| | | | | 600/431 |
| 2015/0105620 A1* | 4/2015 | Oginski | | A61B 1/00121 |
| | | | | 600/112 |
| 2015/0112141 A1* | 4/2015 | Oginski | | A61B 1/00112 |
| | | | | 600/136 |
| 2015/0257629 A1* | 9/2015 | Shahinian | | A61B 1/0669 |
| | | | | 600/106 |
| 2016/0166135 A1* | 6/2016 | Fiset | | A61B 1/126 |
| | | | | 600/101 |
| 2016/0331452 A1* | 11/2016 | Oguni | | A61B 1/0014 |
| 2016/0331454 A1* | 11/2016 | Kobayashi | | A61B 1/0014 |
| 2018/0249899 A1* | 9/2018 | Ouchi | | A61B 1/00133 |

FOREIGN PATENT DOCUMENTS

| | | |
|---|---|---|
| JP | 2016-198673 A | 10/2013 |
| JP | 5543733 B2 | 7/2014 |

* cited by examiner

TREATMENT INSTRUMENT INSERTION TOOL

CROSS REFERENCE TO RELATED APPLICATION

This application is a continuation application of PCT/JP2016/081670 filed on Oct. 26, 2016 and claims benefit of Japanese Application No. 2015-223938 filed in Japan on Nov. 16, 2015, the entire contents of which are incorporated herein by this reference.

BACKGROUND OF THE INVENTION

1. Field of the Invention

The present invention relates to a treatment instrument insertion tool, and more particularly, to a treatment instrument insertion tool which can be attached to an insertion section of an insertion appliance such as an endoscope.

2. Description of the Related Art

Conventionally, endoscopes are widely used in medical and industrial fields. For example, in the medical field, to perform examination of a subject by using an endoscope, a surgeon sometimes performs treatment on a living tissue by using a treatment instrument while looking at an endoscopic image which is displayed on a monitor.

In the case of performing treatment by a treatment instrument, a surgeon has to finely adjust the position of the treatment instrument protruding from a distal end of an insertion section of an endoscope, and normally, a surgeon performs a bending operation of bending a bending portion at the distal end of the insertion section by grasping an operation section of the endoscope with the left hand and operating a bending operation knob or the like provided on the operation section, and performs a forward/backward operation of the insertion section while holding the insertion section with the right hand. Accordingly, a surgeon cannot finely adjust the position of the treatment instrument at the same time as operating the endoscope.

Accordingly, for example, Japanese Patent No. 5543733 proposes a treatment instrument insertion tool for an endoscope, which enables one to perform, with one hand, a forward/backward operation of the treatment instrument while holding the insertion section of the endoscope. According to the proposed treatment instrument insertion tool for an endoscope, a forward/backward operation support tool is attached, through a groove formed to a flexible tube, to a treatment instrument inside the tube, and a surgeon is allowed to move the forward/backward operation support tool along the groove with the hand grasping the insertion section of the endoscope.

SUMMARY OF THE INVENTION

A treatment instrument insertion tool according to an aspect of the present invention is a treatment instrument insertion tool that is attached to an insertion section of an insertion appliance that is inserted into a subject, and that is configured to allow insertion of a treatment instrument into the insertion section, the treatment instrument insertion tool including a main body section configured to allow insertion of the treatment instrument, a guide section that is connectable to a treatment instrument insertion port of the insertion appliance, and that is configured to guide the treatment instrument extending from the main body section into the insertion section through the treatment instrument insertion port, and an operation member that is provided on the main body section, and that is configured to fix the treatment instrument that is inserted in the main body section, by being at least partially elastically deformed, and to perform an operation of moving the treatment instrument forward or backward along a direction of an axis of the treatment instrument and an operation of rotating the treatment instrument around the axis in a fixed state in which the treatment instrument is fixed.

DETAILED DESCRIPTION OF THE PREFERRED EMBODIMENTS

Hereinafter, an embodiment of the present invention will be described with reference to the drawings.
(Configuration of Endoscope)
FIG. 1 is a configuration diagram showing a configuration of an endoscope, according to the present embodiment, to which a treatment instrument insertion tool is attached.

Figure 1:
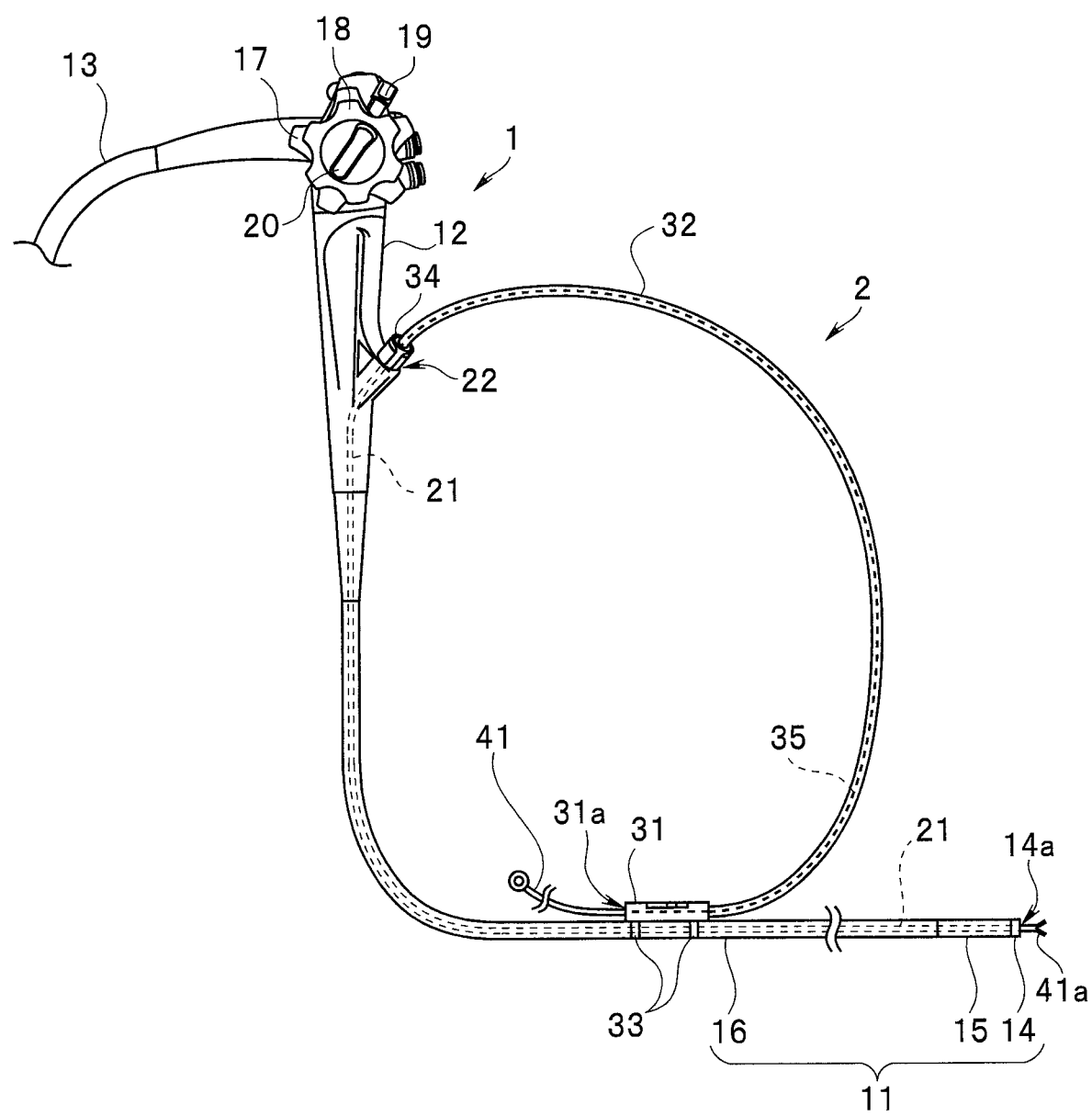
FIG. 1 is a configuration diagram showing a configuration of an endoscope, according to an embodiment of the present invention, to which a treatment instrument insertion tool is attached.

As shown in FIG. 1, an endoscope 1 as an insertion appliance includes an insertion section 11 configured to be inserted into a subject, an operation section 12 provided on the proximal end side of the insertion section 11, and a universal cord 13 extending from the operation section 12. A connector (not shown) for electrically connecting to an external device, not shown, such as a video processor or a light source device is provided at an extended end of the universal cord 13.

A distal end rigid portion 14, a bending portion 15, and a flexible tube portion 16 are continuously provided in the insertion section 11, in this order, from the distal end side, and the insertion section 11 is formed to have an elongated form so that insertion into a subject can be easily performed.

An up-down bending operation knob 17 configured to bend the bending portion 15 of the insertion section 11 in an up-down direction, and a left-right bending operation knob 18 configured to bend the bending portion 15 in a left-right direction are provided on the operation section 12. Furthermore, a fixing lever 19 configured to fix a rotation position of the up-down bending operation knob 17, and a fixing knob 20 configured to fix a rotation position of the left-right bending operation knob 18 are provided on the operation section 12.

The bending portion 15 is bent in four directions of up, down, left and right according to rotation operation of the up-down bending operation knob 17 and the left-right bending operation knob 18. A surgeon may change the observation direction of an image pickup unit provided inside the distal end rigid portion 14 or may adjust the insertion direction of the insertion section 11 inside a subject by bending the bending portion 15.

Moreover, a light guide bundle, not shown, configured to supply illumination light inside a subject is inserted in the universal cord 13, the operation section 12, and the insertion section 11.

A treatment instrument insertion channel 21 allowing insertion of a treatment instrument 41 is formed inside the insertion section 11.

A distal end rigid member is provided inside the distal end rigid portion 14 of the insertion section 11, and an image pickup unit including an image pickup device configured to pick up an image of the inside of a subject is fixed to the distal end rigid member.

Note that, in addition to the image pickup unit, a distal end part of the light guide bundle, not shown, and a distal end part of the treatment instrument insertion channel 21 allowing insertion/removal of a treatment instrument into/from a subject are fixed to the distal end rigid member by well-known fixing means, for example.

Figure 2:
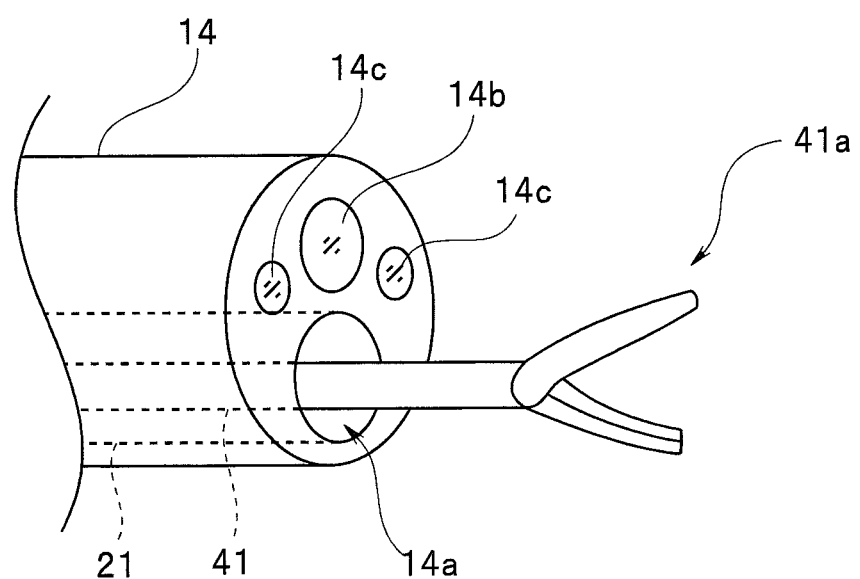
FIG. 2 is a perspective view of a distal end rigid portion 14 according to the embodiment of the present invention.

FIG. 2 is a perspective view of the distal end rigid portion 14. As shown in FIG. 2, a channel opening 14a, an observation window 14b, and two illumination windows 14c are provided in a distal end surface of the distal end rigid portion 14. The channel opening 14a communicates with the treatment instrument insertion channel 21.

An objective lens is arranged at the observation window 14b, and the image pickup unit is disposed at a rear side of the objective lens. The image pickup unit includes an image sensor, which is a solid-state image pickup device such as a CCD or a CMOS.

An image of an examination position in a subject illuminated by illumination light emitted from the two illumination windows 14c is acquired by the image pickup unit, and a surgeon can perform endoscopy examination of the inside of the subject while looking at a subject image that is displayed on a monitor, not shown.

The treatment instrument 41 is capable of protruding or retracting into the channel opening 14a. A treatment instrument insertion port 22 allowing insertion of the treatment instrument 41 is provided in the operation section 12. The treatment instrument 41 includes, at a distal end, an elongated treatment instrument sheath 41b, which is provided with a treatment instrument distal end portion 41a. The treatment instrument insertion port 22 is an opening which communicates with the treatment instrument insertion channel 21, and which allows insertion of a treatment instrument such as a forceps into the treatment instrument insertion channel 21.

A surgeon can perform treatment by inserting the treatment instrument 41 from the treatment instrument insertion port 22 provided in the operation section 12, and by causing the treatment instrument distal end portion 41a of the treatment instrument 41 to protrude from the channel opening 14a. In the case shown in FIG. 2, the treatment instrument 41 that is inserted in the treatment instrument insertion channel 21 is a forceps, and the surgeon can sandwich a living tissue by two sandwiching portions at the treatment instrument distal end portion 41a.

(Configuration of Treatment Instrument Insertion Tool)

As shown in FIG. 1, the treatment instrument insertion tool 2 can be attached to the insertion section 11 of the endoscope 1. The treatment instrument insertion tool 2 includes an operation section 31 and a guide section 32.

The treatment instrument insertion tool 2 is a tool that is attached to the insertion section 11 of the endoscope 1, which is an insertion appliance to be inserted into a subject, and that allows insertion of the treatment instrument 41 into the insertion section 11.

The operation section 31 includes attachment portions 33. In the present embodiment, the attachment portions 33 are formed as parts of a housing, of the operation section 31, configured to attach the operation section 31 to the insertion section 11.

Note that the attachment portions 33 do not have to be parts of the housing of the operation section 31, and may be members which are separate from the housing of the operation section 31 but are fixed to the operation section 31.

The guide section 32 is a flexible tube member, one end of which is connected on the distal end side of the operation section 31 and the other end of which is provided with a connector 34. The connector 34 can be detachably connected to a pipe sleeve of the treatment instrument insertion port 22 of the endoscope 1.

An opening 31a allowing insertion of the treatment instrument 41 is provided on the proximal end side of the operation section 31. The treatment instrument 41 which is inserted from the opening 31a can be inserted into the treatment instrument insertion channel 21 of the endoscope 1 from the connector 34 connected to the treatment instrument insertion port 22, after passing through a treatment instrument insertion channel 35 formed to the operation section 31 and the guide section 32.

That is, the guide section 32 is a tube member which allows insertion of the treatment instrument 41, which is connectable to the treatment instrument insertion port 22, and which guides the treatment instrument 41 extending from a main body section 50 into the insertion section 11 through the treatment instrument insertion port 22.

Accordingly, when a surgeon inserts the treatment instrument 41 from the opening 31a of the operation section 31 in a state where the connector 34 is connected to the treatment instrument insertion port 22, the treatment instrument distal end portion 41a passes through the treatment instrument insertion channels 35 and 21 and protrudes from the channel opening 14a.

Figure 3:
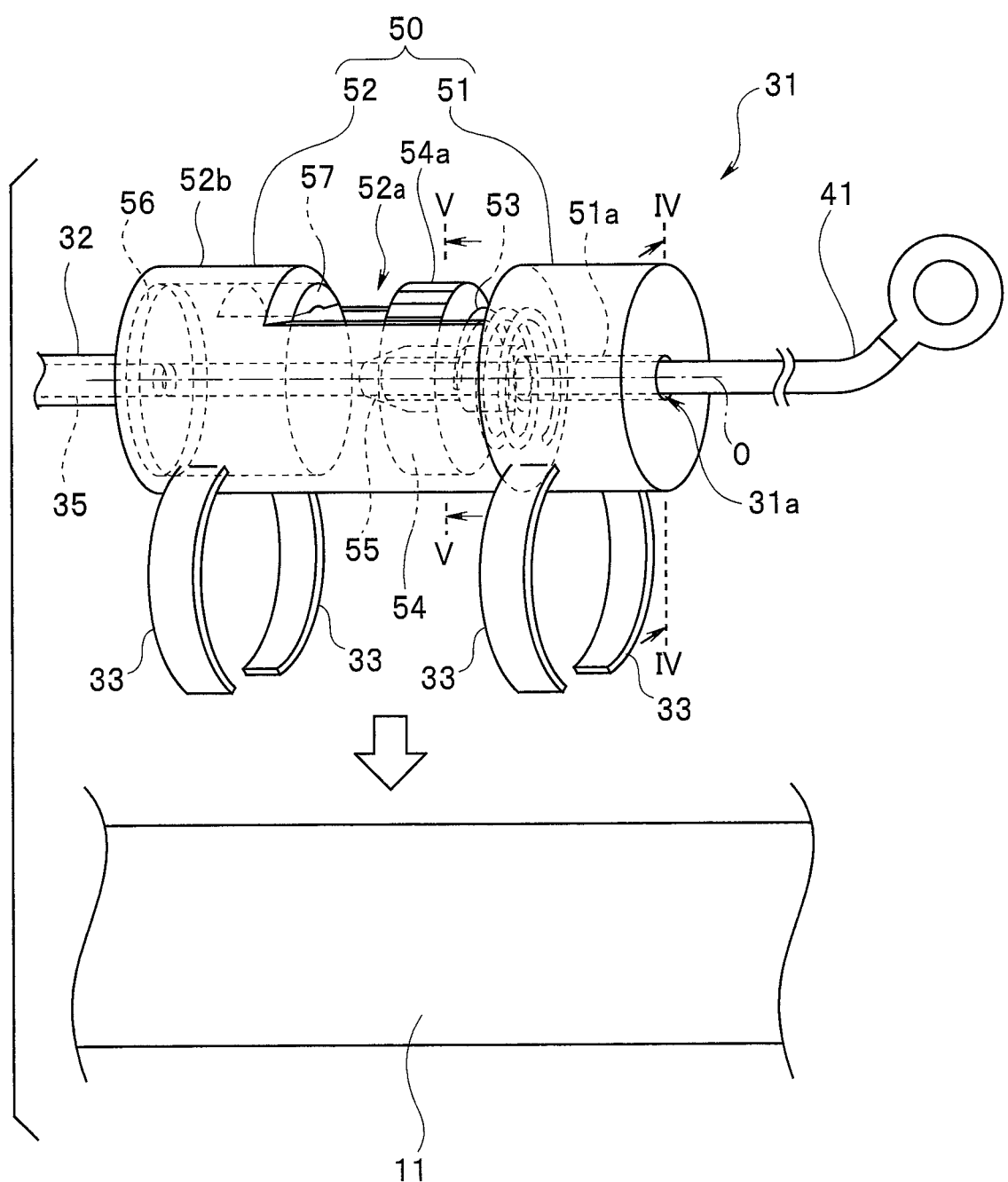
FIG. 3 is a configuration diagram showing a configuration of an operation section of the treatment instrument insertion tool according to the embodiment of the present invention.
Figure 4:
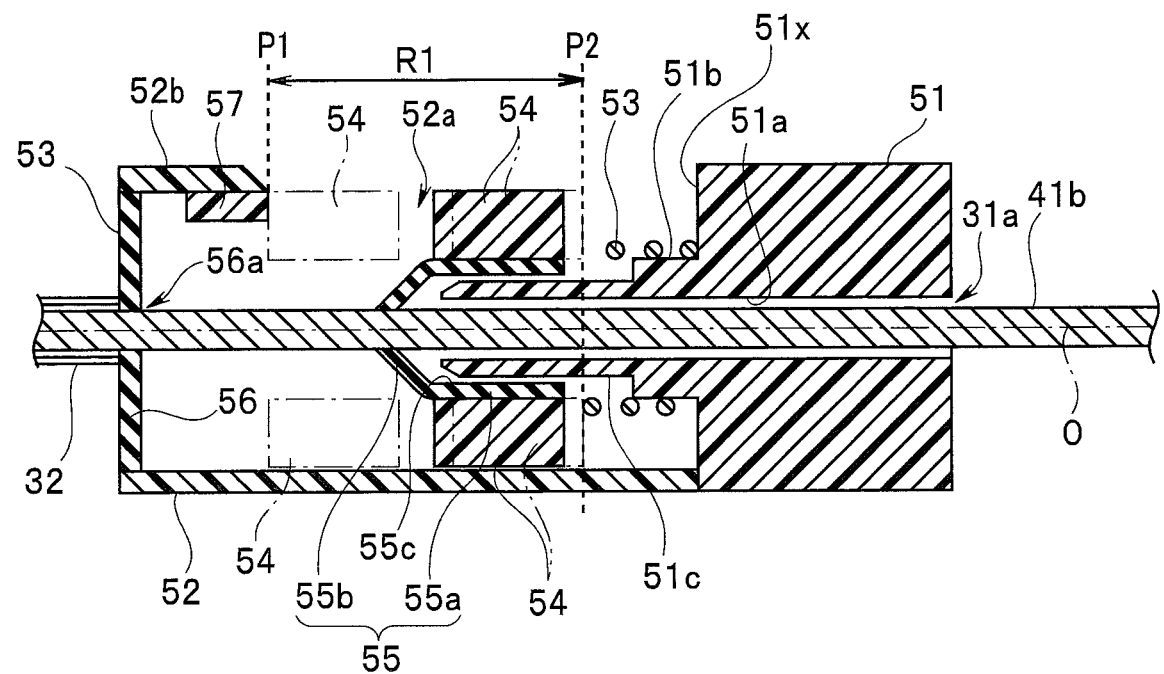
FIG. 4 is a cross-sectional diagram of the operation section, along the line IV-IV in FIG. 3.
Figure 5:
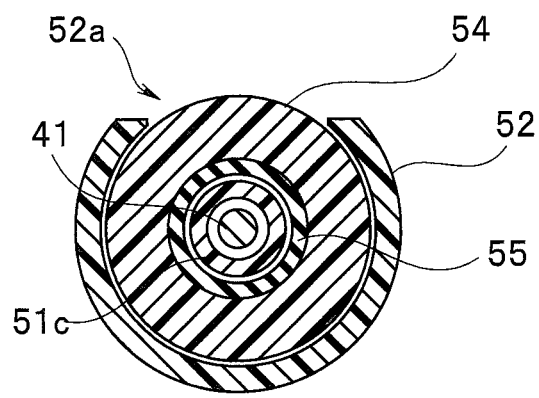
FIG. 5 is a cross-sectional diagram of the operation section, along the line V-V in FIG. 3.

FIG. 3 is a configuration diagram showing a configuration of the operation section of the treatment instrument insertion tool. FIG. 4 is a cross-sectional diagram of the operation section, along the line IV-IV in FIG. 3. FIG. 4 shows a cross-section of the circular cylindrical operation section 31 along a center axis O of the operation section 31. FIG. 5 is a cross-sectional diagram of the operation section, along the line V-V in FIG. 3. FIG. 5 shows a cross-section of the circular cylindrical operation section 31 along a direction that is orthogonal to the center axis O of the operation section 31.

The operation section 31 includes a main body section 50, and the main body section 50 is formed from a first member 51 and a second member 52.

The first member 51 is a circular cylindrical member including a hole 51a formed along the center axis O of a columnar member. A proximal end-side opening of the hole 51a is the opening 31a into which the treatment instrument 41 is to be inserted. Accordingly, an inner diameter d1 of the hole 51a is greater than a diameter of a thickest portion of the treatment instrument 41, that is, a maximum outer diameter d.

A circular cylindrical protruding portion 51b protruding on the distal end side is formed on the distal end side of the first member 51. A circular cylindrical protruding portion 51c protruding on the distal end side is further formed on the distal end side of the circular cylindrical protruding portion 51b. An outer diameter of the circular cylindrical protruding portion 51b is greater than an outer diameter of the circular cylindrical protruding portion 51c.

A tapered portion 51d, an outer diameter of which is reduced toward a distal end, is formed on the distal end side of the circular cylindrical protruding portion 51c.

A center axis O of the first member 51 coincides with axial centers of the circular cylindrical protruding portions 51b and 51c, and the hole 51a is formed along the axial centers of the first member 51, and the circular cylindrical protruding portions 51b and 51c.

A coil spring 53 is fixed to the first member 51 so as to be fitted with the circular cylindrical protruding portion 51b. As shown in FIG. 4, the coil spring 53 is fixed while being inserted over the circular cylindrical protruding portion 51b.

The second member 52 is a circular cylindrical member, and an outer diameter of the second member 52 is the same as an outer diameter of the first member 51. A cut-out portion 52a is formed on the proximal end side of the second member 52, and a distal end portion of the second member 52 is formed into a circular cylindrical portion 52b. That is, the second member 52 constituting the main body section 50 includes a cylindrical section where the cut-out portion 52a is formed, and the treatment instrument 41 is insertable into the cylindrical section.

The main body section 50 is formed by a proximal end portion of the second member 52 being fixed to a distal end portion of the first member 51 by an adhesive or the like.

A circular cylindrical operation member 54, as an operation piece, is disposed inside the second member 52 in a freely fit manner. Surface treatment for slip resistance is applied to an outer surface 54a of the circular cylindrical operation member 54. In this case, knurling for slip resistance is applied to the outer surface 54a.

As shown in FIG. 3, at least a part of the operation member 54 is exposed from the cut-out portion 52a to outside the main body section 50. Operations, such as forward/backward movement along the axial direction of the treatment instrument 41 and rotation around the axis, are performed on an exposed portion of the operation member 54 that is exposed to outside the main body section 50.

A circular cylindrical fixing member 55 is fixed on an inner circumferential surface of the operation member 54 by an adhesive or the like. The fixing member 55 is a rubber member or a metal member which is configured to fix the treatment instrument 41 to the operation member 54, and has a cylindrical shape that surrounds an outer circumferential portion of the treatment instrument 41. Moreover, the operation member 54 has an annular shape that surrounds the fixing member 55.

Note that, in this case, the coil spring 53 is fixed to the first member 51, or more specifically, to the circular cylindrical protruding portion 51b, but the coil spring 53 may alternatively be fixed to the operation member 54, or more specifically, to the proximal end surface of the operation member 54, by fixing means such as an adhesive.

Figure 6:
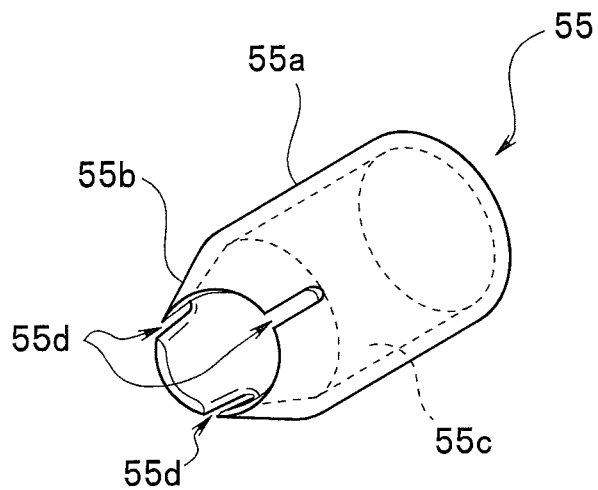
FIG. 6 is a perspective view of a fixing member according to the embodiment of the present invention.

FIG. 6 is a perspective view of the fixing member. FIG. 6 is a perspective view obliquely showing the fixing member 55 from the distal end side. The fixing member 55 includes a circular cylindrical portion 55a, and a narrowed portion 55b, which is formed on the distal end side of the circular cylindrical portion 55a. An outer circumferential portion of the circular cylindrical portion 55a is fixed to an inner circumferential portion of the operation member 54 by an adhesive or the like. A hole 55c is formed in a manner allowing the circular cylindrical protruding portion 51c to be inserted in the hole 55c of the circular cylindrical portion 55a in a freely fitted manner.

The narrowed portion 55b is formed with an inner diameter and an outer diameter being reduced toward a distal end. The narrowed portion 55b includes a plurality (three in this case) of slits 55d, which are formed by making cuts from the distal end side. Note that the number of slits 55d may be one, or two, or four or more.

An inner diameter d2 of a distal end part of the narrowed portion 55b of the fixing member 55 in a natural state is smaller than an outer diameter d3 of the flexible treatment instrument sheath 41b.

Accordingly, when the treatment instrument 41 is inserted into the treatment instrument insertion channel 35, the inner diameter of the distal end part of the narrowed portion 55b, which is an elastic member, is increased to be greater than the inner diameter d2 in the natural state, and the distal end part of the narrowed portion 55b presses an outer circumferential surface of the treatment instrument sheath 41b.

When the treatment instrument 41 is not inserted in the treatment instrument insertion channel 35, the inner diameter of the distal end side of the narrowed portion 55b is the inner diameter d2 in the natural state. That is, the narrowed portion 55b is elastic, and forms an elastic portion that presses the outer circumferential surface of the treatment instrument sheath 41b when the treatment instrument sheath 41b is inserted in the fixing member 55.

A disk-shaped sealing member 56 is fixed on the distal end side of the circular cylindrical portion 52b of the second member 52. The sealing member 56 is an elastic member of rubber or the like, and a hole 56a is formed at a center portion of the sealing member 56. An inner diameter d4 of the hole 56a in a natural state is smaller than the outer diameter d3 of the treatment instrument sheath 41b. Accordingly, when the treatment instrument 41 is inserted in the operation section 31, an inner circumferential surface of the hole 56a of the sealing member 56 closely contacts the outer circumferential surface of the treatment instrument sheath 41b of the treatment instrument 41 to thereby prevent excrement, body fluid or the like from seeping into the operation section 31 from the guide section 32.

The first member 51 and the second member 52 are fixed to each other so that the circular cylindrical protruding portion 51c extending from the first member 51 enters the hole 55c of the circular cylindrical fixing member 55. For this purpose, an outer diameter d5 of the circular cylindrical protruding portion 51c is made smaller than an inner diameter d6 of the hole 55c of the circular cylindrical portion 55a of the fixing member 55, and is made greater than the inner diameter d2 of the distal end part of the narrowed portion 55b of the fixing member 55 in the natural state.

Furthermore, a stopper member 57 configured to prevent the operation member 54 from being fitted entirely into the circular cylindrical portion 52b is fixed on an inner circumferential surface of the circular cylindrical portion 52b of the second member 52 by an adhesive or the like. That is, the stopper member 57 is a member which is configured to restrict movement of the operation member 54 such that the operation member 54 is not fitted entirely into the circular cylindrical portion 52b. FIG. 4 shows, with a dashed-dotted line, that a part of a distal end surface of the operation member 54 is in contact with the stopper member 57 at a position P1.

Note that, in this case, the stopper member 57 is a separate member from the second member 52, but the stopper member 57 may alternatively be formed as a part of the second member 52.

As shown in FIG. 4, a center axis O of the hole 51a of the first member 51 coincides not only with the axial centers of the circular cylindrical protruding portions 51b, 51c, but also with the respective axial centers of the circular cylindrical operation member 54, the circular cylindrical fixing member 55, and the disk-shaped sealing member 56.

One end of the tubular guide section 32 is connected to the distal end side of the second member 52, and is fixed by fixing means such as an adhesive. The guide section 32 is connected and fixed to the operation section 31 so as to allow the treatment instrument 41 inserted into the operation section 31 to pass through the hole 51a, the hole 55c of the fixing member 55, and the hole 56a of the sealing member 56, and to enter the guide section 32.

Accordingly, the treatment instrument insertion channel 35 is formed from the opening 31a of the first member 51 to the distal end of the guide section 32, and the treatment instrument 41 is allowed to be inserted into the treatment instrument insertion channel 35.

The operation member 54 is capable of moving inside the operation section 31, along the axial direction of the main body section 50, but when the operation member 54 moves, inside the operation section 31, across a predetermined position toward the proximal end side, the operation member 54 contacts a distal end portion of the coil spring 53. When the operation member 54 further moves from the predetermined position toward the proximal end side, the coil spring 53 biases the operation member 54 toward the distal end side.

More specifically, as shown in FIG. 4 with a dashed-two dotted line, when the proximal end surface of the operation member 54 reaches a position indicated by a position P2, the proximal end surface of the operation member 54 contacts the distal end portion of the coil spring 53. When the surgeon moves the operation member 54 to the proximal end side and the proximal end surface of the operation member 54 moves across the position P2, the operation member 54 is pushed back toward the distal end side by the biasing force of the coil spring 53, and the surgeon feels the force of pushing back on a finger.

Note that in a case where the coil spring 53 is fixed to the operation member 54 by fixing means such as an adhesive, when the proximal end surface of the operation member 54 reaches the position indicated by the position P2, the proximal end portion of the coil spring 53 contacts a distal end surface 51x of the first member 51. At this time, the surgeon feels, on a finger, the force of the operation member 54 being pushed back toward the distal end side by the biasing force of the coil spring 53.

Accordingly, the surgeon may operate the operation member 54 with a finger and pull the operation member 54 against the biasing force of the coil spring 53 to thereby move the operation member 54 toward the proximal end side of the operation section 31 across the position P2, but when the surgeon removes the finger from the operation member 54, a biasing force is applied to the operation member 54 by the coil spring 53 toward the distal end side of the operation section 31, or in other words, away from the proximal end side.

When the operation member 54 is not being biased by the coil spring 53 as a compression spring, that is, when the operation member 54 is not moved across the position P2 toward the proximal end side of the operation section 31, an inner circumferential surface of the distal end part of the narrowed portion 55b of the fixing member 55 is in close contact with an outer surface of the treatment instrument sheath 41b of the treatment instrument 41, and the operation member 54 presses the treatment instrument sheath 41b of the treatment instrument 41 to hold, i.e., fix, the treatment instrument sheath 41b.

In other words, a state where the fixing member 55 is in close contact with the treatment instrument sheath 41b of the treatment instrument 41 is achieved, and the treatment instrument 41 is placed in a state where the treatment instrument 41 moves in coordination with the movement of the operation member 54. In a range R1 from the position P1 to the position P2 described above, the surgeon may move the treatment instrument 41 by moving the operation member 54, without feeling the biasing force of the coil spring 53. More specifically, the treatment instrument 41 may be moved forward/backward by moving the operation member 54 forward/backward in the range R1, along the center axis O of the operation section 31, and the treatment instrument 41 may be rotated around the axis by rotating the operation member 54 around the center axis O.

When the operation member 54 moves across the position P2 toward the proximal end side of the operation section 31 while compressing the coil spring 53, the fixing member 55 also moves, together with the operation member 54, toward the proximal end side of the operation section 31. When the fixing member 55 moves to the proximal end side of the operation section 31 and moves closer to the first member 51 than a certain position, the inner circumference surface of the distal end part of the narrowed portion 55b is increased by the circular cylindrical protruding portion 51c of the first member 51, and the inner circumferential surface of the distal end part of the narrowed portion 55b will no longer closely contact the outer surface of the treatment instrument sheath 41b of the treatment instrument 41.

When the inner circumferential surface of the distal end part of the narrowed portion 55b is no longer in close contact with the outer surface of the treatment instrument sheath 41b of the treatment instrument 41, the movement along the direction of the center axis O and the rotation around the center axis O of the treatment instrument 41 are no longer restricted. That is, the circular cylindrical protruding portion 51c releases the fixed state of the treatment instrument 41 to the fixing member 55. The circular cylindrical protruding portion 51c configures a fixation release portion that is provided on the main body section 50, and that releases the treatment instrument 41 from the fixed state.

More specifically, when the operation member 54 is moved toward the proximal end side of the operation section 31 with the proximal end surface of the operation member 54 moving across the position P2, and the operation member 54 reaches a certain position, the circular cylindrical protruding portion 51c starts increasing the inner circumference surface of the distal end part of the narrowed portion 55b, and when the operation member 54 is further moved toward the proximal end side of the operation section 31, the inner circumferential surface of the distal end part of the narrowed portion 55b stops being in contact with the treatment instrument sheath 41b of the treatment instrument 41.

Figure 7:
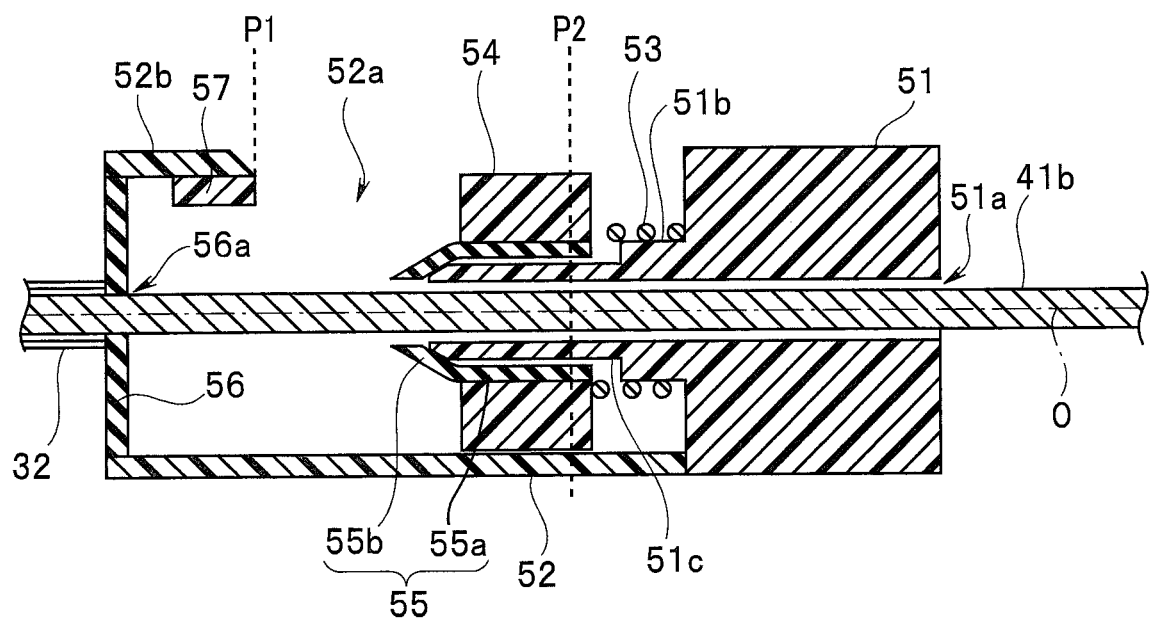
FIG. 7 is a cross-sectional diagram of the operation section according to the embodiment of the present invention, along the line IV-IV in FIG. 3, where an inner circumference surface of a distal end part of a narrowed portion is increased by a circular cylindrical protruding portion 51c.

FIG. 7 is a cross-sectional diagram of the operation section, along the line IV-IV in FIG. 3, where the inner circumference surface of the distal end part of the narrowed portion is increased by the circular cylindrical protruding portion 51c.

When the outer circumferential surface of the treatment instrument sheath 41b is no longer pressed by the narrowed portion 55b, and the fixed state of the treatment instrument 41 to the fixing member 55 is released, the surgeon may pull out the treatment instrument 41 with no resistance.

Note that when the operation member 54 moves across the position P2 during the forward/backward operation of the treatment instrument 41, the surgeon may feel, on the hand, that the amount of operation force is increased by the biasing force of the coil spring 53, and thus, fixation of the treatment instrument 41 to the fixing member 55 may be prevented from being released during the forward/backward operation of the treatment instrument 41 against the intention of the surgeon.

As described above, the operation member 54 to which the fixing member 55 is fixed configures an operation section that is provided on the main body section 50, and that is configured to allow fixing of the treatment instrument 41 inserted in the main body section 50, by being at least partially elastically deformed, and to perform, with respect to the treatment instrument 41, a forward/backward operation along the axial direction and a rotation operation around the axis, in a fixed state where the treatment instrument 41 is fixed.

The operation section includes the fixing member 55 configured to fix the treatment instrument 41 by pressing the outer circumferential portion of the treatment instrument 41 by being at least partially elastically deformed, and the operation member 54 as an operation piece that is fixed to the fixing member 55.

Moreover, when the operation piece is operated so as to move the fixing member 55 pressing the outer circumferential portion of the treatment instrument 41 toward the circular cylindrical protruding portion 51c, the circular cylindrical protruding portion 51c as the fixation release portion enters between the fixing member 55 and the outer circumferential portion of the treatment instrument 41 to release the fixed state.

Furthermore, when the fixing member 55 pressing the outer circumferential portion of the treatment instrument 41 is moved toward the circular cylindrical protruding portion 51c, the coil spring 53 as a biasing member biases the operation member 54 in a direction of separating the fixing member 55 away from the circular cylindrical protruding portion 51c.

As shown in FIG. 3, the operation section 31 can be attached to the insertion section 11 by the attachment portions 33.

More specifically, two arc-shaped portions 33a configured to be attached to the insertion section 11 of the endoscope 1 are formed to the first member 51, which is made of resin. In the same manner, two arc-shaped portions 33b configured to be attached to the insertion section 11 of the endoscope 1 are formed to the second member 52, which is made of resin. Each arc-shaped portion 33a, 33b is elastic. The two arc-shaped portions 33a and 33b are configured to be attached to the insertion section 11 by inner surfaces of the respective arc-shaped portions 33a, 33b covering and coming into contact with an outer circumferential portion of the insertion section 11.

Accordingly, as shown by an arrow in FIG. 3, the arc-shaped portions 33a and 33b configuring the attachment portions 33 can be detachably attached to the insertion section 11 in a manner sandwiching the insertion section 11 like clips, and also, can be attached to the insertion section 11 while allowing the operation section 31 to be moved in the axial direction of the insertion section 11. That is, the attachment portions 33 configure attachment portions that detachably attach the main body section 50 to the insertion section 11.

Note that the attachment portion 33 may be a belt that can be wound around the insertion section 11 in a detachable manner.

(Action)

Next, an action of the treatment instrument insertion tool will be described.

A surgeon performs endoscopy examination by inserting the insertion section 11 into a subject, and can observe the inside of the subject by looking at an endoscopic image, and can also treat a lesion by using the treatment instrument 41.

Before starting endoscopy examination or during examination, the surgeon attaches the operation section 31 to the insertion section 11 by the attachment portions 33, and attaches and fixes the connector 34 of the guide section 32 to the treatment instrument insertion port 22. Then, the surgeon inserts the treatment instrument 41 from the opening 31a, and positions the treatment instrument distal end portion 41a near the channel opening 14a of the distal end rigid portion 14 of the insertion section 11.

For example, in the case of examining the large intestine, the surgeon inserts the distal end rigid portion 14 of the insertion section 11 deep into the large intestine, and then, performs endoscopy examination while pulling out the insertion section 11.

When a position inside the subject where treatment should be performed using the treatment instrument 41 is found during the examination, the surgeon moves the operation section 31 near, for example, the thumb of the hand, such as the right hand, grasping the insertion section 11 in a state where the distal end rigid portion 14 of the insertion section 11 is brought close to the position.

As described above, the attachment portions 33 are attached to the insertion section 11 while being capable of moving in the axial direction of the insertion section 11, and thus, the surgeon can move the operation section 31 along the axial direction of the insertion section 11 and move the operation section 31 near the hand grasping the insertion section 11.

After moving the operation section 31 near the hand grasping the insertion section 11, the surgeon grasps the treatment instrument 41 protruding from the opening 31a on the proximal end side of the operation section 31 of the treatment instrument insertion tool 2, and causes the treatment instrument distal end portion 41a to protrude from the channel opening 14a of the distal end rigid portion 14 of the insertion section 11.

Next, the surgeon brings the distal end rigid portion 14 of the insertion section 11 close to the lesion while looking at an endoscopic image displayed on a monitor, and secures a field of view of the endoscopic image while positioning the distal end rigid portion 14 at a position and an attitude which are convenient for treating the lesion, by moving the insertion section 11 forward or backward or by bending the bending portion 15, for example.

While maintaining the position and the attitude which are convenient for treating the lesion, the surgeon can move the treatment instrument distal end portion 41a closer to or away from the lesion by moving the operation member 54 forward or backward along the center axis O of the operation section 31 within the range R1 with the thumb of the hand (for example, the right hand) grasping the insertion section 11.

Moreover, while maintaining the position and the attitude which are convenient for treating the lesion and securing the field of view of the endoscopic image, the surgeon can change the orientation of the treatment instrument distal end portion 41a by rotating the operation member 54, which is within the range R1, around the center axis O of the operation section 31 with the thumb of the hand (for example, the right hand) grasping the insertion section 11. For example, the surgeon can operate the operation member 54 with a finger of the grasping hand while continuing to grasp the insertion section 11 with the hand grasping the insertion section 11, and can change the opening/closing direction of the two sandwiching members of a forceps, which is a treatment instrument, to an orientation that allows the lesion to be easily grasped.

Accordingly, the surgeon can operate the operation member 54 of the operation section 31 in a state of grasping the insertion section 11 and with no shift in the secured field of view of the endoscopic image, and can thereby easily perform the forward/backward operation and the rotation operation on the treatment instrument 41.

When the surgeon wants to cause the treatment instrument distal end portion 41a to further protrude from the channel opening 14a toward the distal end side, or to cause the treatment instrument distal end portion 41a to further retract from the channel opening 14a toward the proximal end side, or to cause the treatment instrument distal end portion 41a to retract from within the operation section 31 to the guide section 32, the surgeon moves the operation member 54 toward the proximal end side of the operation section 31 against the biasing force of the coil spring 53, and can thereby release the fixation of the treatment instrument 41 to the operation member 54. In this case, when moving the operation member 54 toward the proximal end side of the operation section 31, the surgeon can recognize the release position of fixation of the treatment instrument 41 by feeling, with the finger, the biasing force of the coil spring 53 by a change in the amount of operation force of the operation member 54.

Next, modifications of the present embodiment will be described.

(First Modification)

Figure 8:
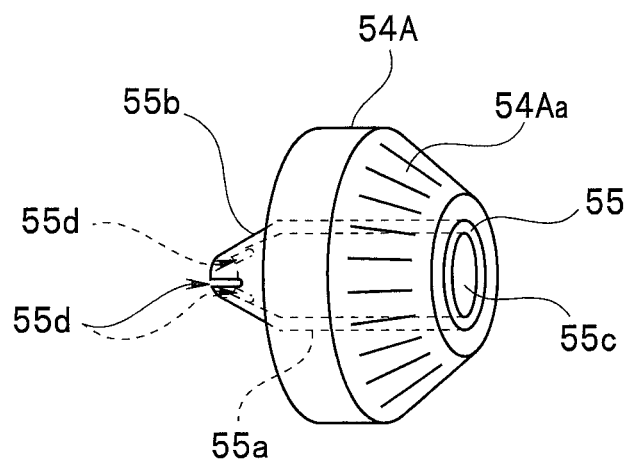
FIG. 8 is a perspective view of an operation member of the operation section of the treatment instrument insertion tool, according to a first modification of the embodiment of the present invention.

In a first modification, the operation member 54 of the operation section 31 may have a shape as shown in FIG. 8.

FIG. 8 is a perspective view of a modification of the operation member of the operation section of the treatment instrument insertion tool. An operation member 54A of the first modification includes an inclined surface 54Aa on the proximal end side. Accordingly, a surgeon may easily operate the operation member 54A by placing a finger on the inclined surface 54Aa.

(Second Modification)

Figure 9:
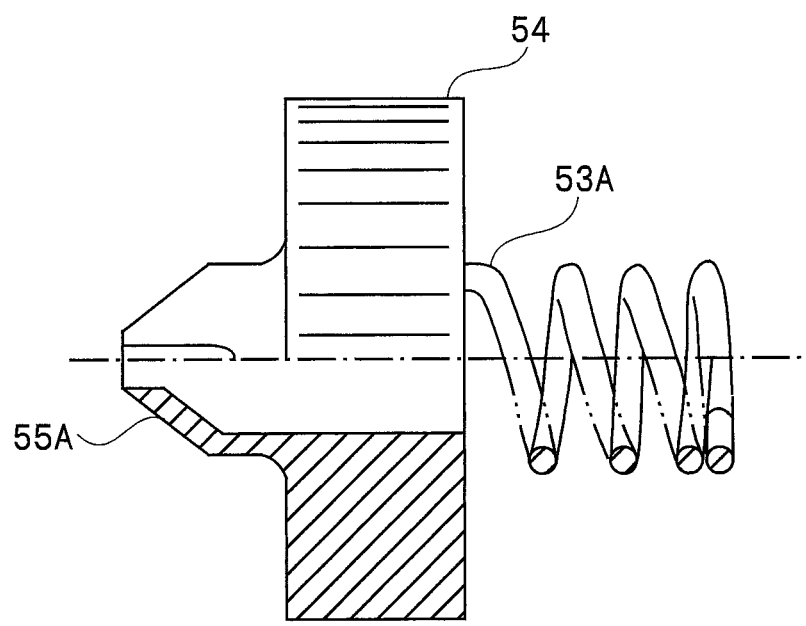
FIG. 9 is a partial cross-sectional diagram showing a modification of the operation member of the operation section of the treatment instrument insertion tool, according to a second modification of the embodiment of the present invention.

In a second modification, the operation member may be a member as shown in FIG. 9.

FIG. 9 is a partial cross-sectional diagram showing a modification of the operation member of the operation section. As shown in FIG. 9, a fixing portion 55A having the same function as the fixing member 55 may be integrally formed with the operation member 54, or a biasing portion 53A having a spring shape, for example, may be integrally formed with the operation member 54.

That is, both the fixing portion 55A and the biasing portion 53A may be integrally formed with the operation member 54, or one of the fixing portion 55A and the biasing portion 53A may be integrally formed with the operation member 54.

The operation member 54 with which such other portion is integrally formed may be of metal or of resin.

(Third Modification)

Figure 10:
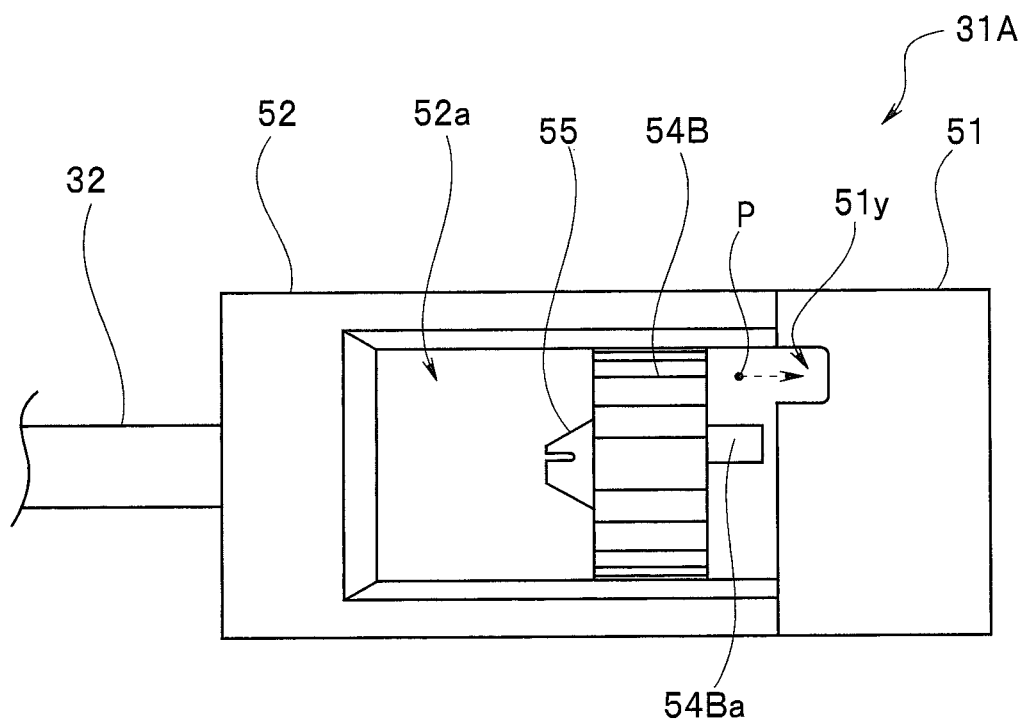
FIG. 10 is a top view of an operation section of the treatment instrument insertion tool, according to a third modification of the embodiment of the present invention.

Further note that the operation section may have a configuration as shown in FIG. 10.

FIG. 10 is a top view of the operation section, showing a modification of the operation section of the treatment instrument insertion tool. An operation section 31A according to the modification includes a projecting portion 54Ba on the proximal end side of an operation member 54B. The projecting portion 54Ba is provided protruding in the proximal end direction from a proximal end surface of the operation member 54B, which is disk-shaped. The projecting portion 54Ba is provided near an outer circumferential portion of the operation member 54B.

A recessed portion 51y where the projecting portion 54Ba can enter is formed to the first member 51. The operation member 54B is capable of rotating around the axis, and thus, the projecting portion 54Ba can be caused to enter the recessed portion 51y by rotating the operation member 54B and moving the operation member 54B to the proximal end side when the projecting portion 54Ba is at a position of a point P.

In contrast, when the projecting portion 54Ba is not at the position of the point P, even if the operation member 54B is moved toward the proximal end side, the projecting portion 54Ba abuts against a distal end surface of the first member 51 and cannot enter the recessed portion 51y.

Accordingly, to realize a non-sandwiched state in which the treatment instrument 41 is not sandwiched by the narrowed portion 55b of the fixing member 55 after realizing a sandwiched state in which the treatment instrument 41 is sandwiched by the narrowed portion 55b, the surgeon has to place the projecting portion 54Ba at the position of the point P.

In other words, if the surgeon does not place the projecting portion 54Ba at the position of the point P, the treatment instrument 41 is kept in a fixed state in which the treatment instrument 41 is sandwiched and fixed by the narrowed portion 55b of the fixing member 55, and the operation member 54B is not caused to move toward the proximal end side even if the surgeon unintentionally performs an operation of moving the operation member 54B toward the proximal end side with a finger, unless the projecting portion 54Ba is at the position of the point P. If the projecting portion 54Ba is not at the position of the point P, a non-fixed state in which the treatment instrument 41 is not sandwiched by the narrowed portion 55b is not caused.

Therefore, according to the present modification, the treatment instrument 41 may be prevented from being easily placed in the non-fixed state due to an unintentional operation by the surgeon.

As described above, according to the embodiment and each modification described above, a treatment instrument insertion tool can be provided which allows a surgeon to perform an operation of rotating a treatment instrument, used together with an insertion appliance, around the axis without taking the hand off an insertion section the hand is grasping.

The present invention is not limited to the embodiment described above, and various changes and alterations can be made within the scope of the present invention.

What is claimed is:

1. A treatment instrument insertion tool that is attached to an insertion section of an insertion appliance that is inserted into a subject, and that is configured to allow insertion of a treatment instrument into the insertion section, the treatment instrument insertion tool comprising:
    a main body configured to allow insertion of the treatment instrument;
    a guide member that is connectable to a treatment instrument insertion port of the insertion appliance, and that is configured to guide the treatment instrument extending from the main body into the insertion section through the treatment instrument insertion port;
    an operation member that is provided on the main body, and that is configured to fix the treatment instrument that is inserted in the main body, by being at least partially elastically deformed, and to perform an operation of moving the treatment instrument forward or backward along a direction of an axis of the treatment instrument and an operation of rotating the treatment instrument around the axis in a fixed state in which the treatment instrument is fixed; and
    a fixation release member that is provided on the main body, and that is configured to release the treatment instrument from the fixed state,
    wherein the operation member includes an operation piece and a fixing member that is fixed to the operation piece, the fixing member being configured to fix the treatment instrument by pressing an outer circumferential portion of the treatment instrument by being at least partially elastically deformed, and
    the fixation release member is provided so as to release the fixed state by entering between the fixing member and the outer circumferential portion of the treatment instrument, when the operation piece is operated such that the fixing member pressing the outer circumferential portion of the treatment instrument is moved toward the fixation release member.

2. The treatment instrument insertion tool according to claim 1, further comprising an attachment portion configured to attach the main body to the insertion section of the insertion appliance.

3. The treatment instrument insertion tool according to claim 1, comprising a biasing member that is configured to bias the operation piece in a direction of separating the fixing member away from the fixation release member, when the fixing member pressing the outer circumferential portion of the treatment instrument is moved in a direction toward the fixation release member.

4. The treatment instrument insertion tool according to claim 1, wherein
    the guide member is a tube member configured to allow insertion of the treatment instrument, and
    one end of the tube member is connected to the main body, and another end is connectable to the treatment instrument insertion port of the insertion appliance.

5. A treatment instrument insertion tool, that is attached to an insertion section of an insertion appliance that is inserted into a subject, and that is configured to allow insertion of a treatment instrument into the insertion section, the treatment instrument insertion tool comprising:
    a main body configured to allow insertion of the treatment instrument;
    a guide member that is connectable to a treatment instrument insertion port of the insertion appliance, and that is configured to guide the treatment instrument extending from the main body into the insertion section through the treatment instrument insertion port;
    an operation member that is provided on the main body, and that is configured to fix the treatment instrument that is inserted in the main body, by being at least partially elastically deformed, and to perform an operation of moving the treatment instrument forward or backward along a direction of an axis of the treatment instrument and an operation of rotating the treatment instrument around the axis in a fixed state in which the treatment instrument is fixed; and
    a fixation release member that is provided on the main body, and that is configured to release the treatment instrument from the fixed state,
    wherein the operation member includes an operation piece and a fixing member that is fixed to the operation piece, the fixing member being configured to fix the treatment instrument by pressing an outer circumferential portion of the treatment instrument by being at least partially elastically deformed, and
    the operation of moving the treatment instrument forward or backward along the direction of the axis and the operation of rotating the treatment instrument around the axis are performed by operation of the operation piece.

6. The treatment instrument insertion tool according to claim 5, wherein
    the fixing member has a shape that surrounds the outer circumferential portion of the treatment instrument, and
    the operation piece has an annular shape that surrounds the fixing member.

7. The treatment instrument insertion tool according to claim 6, wherein the shape that surrounds the outer circumferential portion of the treatment instrument is a cylindrical shape.

8. The treatment instrument insertion tool according to claim 7, wherein the outer circumferential portion of the treatment instrument includes one or more slits.

9. The treatment instrument insertion tool according to claim 5, wherein the guide member is a tube member configured to allow insertion of the treatment instrument, and one end of the tube member is connected to the main body, and another end is connectable to the treatment instrument insertion port of the insertion appliance.

10. A treatment instrument insertion tool, that is attached to an insertion section of an insertion appliance that is inserted into a subject, and that is configured to allow insertion of a treatment instrument into the insertion section, the treatment instrument insertion tool comprising:
    a main body configured to allow insertion of the treatment instrument;
    a guide member that is connectable to a treatment instrument insertion port of the insertion appliance, and that is configured to guide the treatment instrument extending from the main body into the insertion section through the treatment instrument insertion port;
    an operation member that is provided on the main body, and that is configured to fix the treatment instrument that is inserted in the main body, by being at least partially elastically deformed, and to perform an operation of moving the treatment instrument forward or backward along a direction of an axis of the treatment instrument and an operation of rotating the treatment instrument around the axis in a fixed state in which the treatment instrument is fixed; and a fixation release member that is provided on the main body, and that is configured to release the treatment instrument from the fixed state.

wherein the main body includes a cylindrical portion in which a cut-out portion is formed, the treatment instrument is insertable into the cylindrical portion, the operation member is disposed inside the cylindrical portion, at least a part of the operation member is exposed to outside the main body from the cut-out portion, and the operation of moving the treatment instrument forward or backward along the direction of the axis and the operation of rotating the treatment instrument around the axis are performed on an exposed portion of the operation member that is exposed to outside the main body.

11. The treatment instrument insertion tool according to claim 10, wherein the guide member is a tube member configured to allow insertion of the treatment instrument, and one end of the tube member is connected to the main body, and another end is connectable to the treatment instrument insertion port of the insertion appliance.

\* \* \* \* \*